United States Patent
Stan

(10) Patent No.: US 8,609,927 B2
(45) Date of Patent: Dec. 17, 2013

(54) CAVEOLIN 1-REPORTER PROTEIN KNOCK-IN MOUSE

(75) Inventor: Radu V. Stan, Lebanon, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 13/319,543

(22) PCT Filed: May 21, 2010

(86) PCT No.: PCT/US2010/035706
§ 371 (c)(1),
(2), (4) Date: Nov. 9, 2011

(87) PCT Pub. No.: WO2010/138397
PCT Pub. Date: Dec. 2, 2010

(65) Prior Publication Data
US 2012/0060232 A1    Mar. 8, 2012

Related U.S. Application Data

(60) Provisional application No. 61/181,832, filed on May 28, 2009.

(51) Int. Cl.
*A01K 67/027* (2006.01)
*A01K 67/033* (2006.01)

(52) U.S. Cl.
USPC .................................. 800/18; 800/22

(58) Field of Classification Search
None
See application file for complete search history.

(56) References Cited

U.S. PATENT DOCUMENTS

| | | | |
|---|---|---|---|
| 2005/0036986 A1 | 2/2005 | Thompson | 424/93.2 |
| 2008/0132508 A1 | 6/2008 | Kester | 514/237.8 |
| 2009/0035784 A1 | 2/2009 | Ioannou | 435/7.1 |
| 2009/0075875 A1 | 3/2009 | Hoffman | 514/8.9 |

OTHER PUBLICATIONS

Manis, J.P. "Knock Out, Knock In, Knock Down—Genetically Manipulated Mice and the Nobel Prize" New England Journal of Medicine 2007 357 (24):2426-2429.

*Primary Examiner* — Scott Long
(74) *Attorney, Agent, or Firm* — Licata & Tyrrell, P.C.

(57) ABSTRACT

The present invention embraces a transgenic mouse whose genome harbors a nucleic acid molecule encoding caveolin-1 fused in-frame with a reporter. To control expression of the Cav1-reporter, the nucleic acid molecule further includes a selectable marker expression cassette flanked by recombinase target sites in such a manner that, upon exposure to recombinase, said selectable marker expression cassette is excised from said nucleic acid molecule.

7 Claims, No Drawings

CAVEOLIN 1-REPORTER PROTEIN KNOCK-IN MOUSE

This application is a U.S. National Stage Application of PCT/US2010/035706 filed May 21, 2010 and claims the benefit of priority of U.S. Provisional Application No. 61/181,832, filed May 28, 2009, the contents of each of which are incorporated herein by reference in their entirety.

INTRODUCTION

This invention was made with government support under grant numbers R01 HL083249 and R01 HL065418 awarded by the National Institutes of Health. The government has certain rights in the invention.

BACKGROUND OF THE INVENTION

Caveolin 1 (Cav1) is the gene product of the Cav1 locus. Cav1 is a member of the caveolin family of proteins along with Cav2 and Cav3 as well as some invertebrate caveolins. Cav1 is a phosphoprotein with a structural role in the formation of caveolae, organelles with multiple but controversial assigned functions. Loss of Cav1 results in severe dislipidemia both in mouse and humans. It also leads to a cardiovascular phenotype with dilative cardiomyopathy and pulmonary hypertension. In addition, loss of Cav1 protein results in a type II diabetes syndrome with hyperglyceridemia, hyperinsulinemia and decreased tolerance to glucose. Caveolin 1 is involved in multiple signal transduction pathways. It is believed to be a tumor suppressor, as well as an angiogenesis inhibitor. Caveolin 1 is involved in mechanical flow sensing as well as in inflammation and permeability.

SUMMARY OF THE INVENTION

The present invention is a transgenic mouse whose genome harbors a nucleic acid molecule encoding caveolin-1 fused in-frame with a reporter, wherein said nucleic acid molecule further includes a selectable marker expression cassette flanked by recombinase target sites in such a manner that, upon exposure to recombinase, said selectable marker expression cassette is excised from said nucleic acid molecule. In one embodiment, the recombinase is Cre and the recombinase target sites are lox P sequences. In another embodiment, the recombinase is Flp and the recombinase target sites are Frt sequences. In certain embodiments, the reporter protein is a fluorescent protein. In particular embodiments the selectable marker expression cassette is neomycin expression cassette. Transgenic mice wherein the endogenous caveolin-1 gene has been knocked out are also embraced by this invention.

A method for generating a mouse expressing caveolin-1 in a time- or tissue-specific manner is also provided by mating the transgenic Cav1-reporter mouse to a mouse whose genome harbors a nucleic acid molecule encoding a recombinase under the control of a time- or tissue-specific promoter, thereby generating a mouse expressing caveolin-1 in a time- or tissue-specific manner.

DETAILED DESCRIPTION OF THE INVENTION

Using heterologous recombination in mice, a Caveolin 1 (Cav1) knock-in mouse has now been generated. The knock-in construct used in the generation of the transgenic mouse of the invention was composed of nucleic acids encoding Cav1 fused in-frame with nucleic acids encoding the reporter protein GFP. The knock-in construct further included the marker expression cassette encoding the neomycin resistant gene flanked by loxP recombinase target sites, wherein the neomycin expression cassette disrupted the Cav1 locus of the knock-in construct, thereby resulting in a Cav1 null allele.

Using the transgenic mouse of the invention, Cav1-GFP expression can be controlled in a time- and/or tissue-specific manner by crossing the Cav1 knock-in mouse with a transgenic mouse expressing a recombinase, such as Cre recombinase, the expression of which is under the control of a time- and/or tissue-specific promoter. Transgenic mice of the invention can express endogenous Cav1 or alternatively lack endogenous Cav1 expression so that rescue experiments can be performed, wherein the Cav1-GFP protein is expressed in time- and/or tissue-specific manner.

The mice of the present invention find application in in vivo studies of vascular permeability and in analyzing cardiovascular functions and diseases where caveolae have been implicated. Such diseases include, but are not limited to atherosclerosis and tumor angiogenesis. In addition, caveolae have been implicated in the formation of fat (adipose) tissue, and the Cav1 knock-in mice on could be used to evaluate the role of caveolin 1 in the regulation of fat deposit formation. Moreover, transgenic mice of the invention could be used in screening assays to identify agents that modulate the expression of caveolin 1.

For the purposes of the present invention, caveolin 1 is the scaffolding protein that is the main component of the caveolae plasma membranes found in most cell types. The protein links integrin subunits to the tyrosine kinase FYN, an initiating step in coupling integrins to the Ras-ERK pathway and promoting cell cycle progression. The caveolin 1 gene is a tumor suppressor gene candidate and a negative regulator of the Ras-p42/44 MAP kinase cascade. The Cav1 to be introduced into the transgenic mouse can be from any suitable source including, but not limited to, mouse, rat, human, monkey, and the like. Nucleic acids encoding these proteins are well-known in the art. For example, human Cav1 is available under GENBANK Accession No. NP_001744, mouse Cav1 is available under Accession No. NP_031642; and rat Cav1 is available under Accession No. NP_113744. In particular embodiments, the mouse Cav1 protein is employed.

To facilitate detection of transgenic Cav1 expression in the transgenic mouse of the invention, the nucleic acids encoding Cav1 are fused in-frame with nucleic acids encoding a reporter protein thereby creating a Cav1-reporter fusion protein. In-frame fusions of nucleic acids to create fusion proteins are routinely practiced in the art and can be accomplished by conventional restriction enzyme and/or overlap PCR technologies.

A reporter protein of the invention includes fluorescent proteins and enzymes detectable by a histochemical process. Exemplary enzymes detectable by a histochemical process include, but are not limited to β-galactosidase, β-glucuronidase, alkaline phosphatase, luciferase, alcohol dehydrogenase, chloramphenicol-acetyl transferase, and peroxidase. The substrates to be used with these specific enzymes are generally chosen for the production, upon hydrolysis by the corresponding enzyme, of a detectable color change. Substrate can be soluble or insoluble, added into the culture medium of a cell or tissue isolated from a transgenic mouse of the invention, or present in the host cell, depending upon the chosen method. For example, 5-bromo-4-chloro-3-indoyl phosphate/nitroblue tetrazolium is suitable for use with alkaline phosphatase conjugates; for peroxidase conjugates, 1,2-phenylenediamine-5-aminosalicylic acid, 3,3,5,5,-tetramethylbenzidine, tolidine or dianisidine are commonly used.

Autofluorescent proteins such as green fluorescence protein (GFP), the enhanced green fluorescence protein (eGFP), the red fluorescence protein (RFP), the blue fluorescence protein (BFP), the yellow fluorescence protein (YFP) and fluorescent variants of these proteins offer particular advantages in the transgenic mouse of this invention in that substrates are not required. Accordingly, particular embodiments embrace fusion of Cav1 to an autofluorescent reporter protein.

According to the invention, the Cav1 open reading frame has inserted therein a selectable marker expression cassette to inactivate the Cav1-reporter transgene. For the purposes of the present invention, a selectable marker expression construct is a nucleic acid molecule coding for and capable of expressing a selectable marker protein. In this respect, the selectable marker expression construct includes all the necessary regulatory sequences (e.g., promoter, terminator, and the like) to regulate expression of the selectable marker protein. Selectable marker expression constructs which can be used in accordance with the present invention include, for example, drug-resistance genes, such as the neomycin-resistance gene (selected by G418 resistance), the thymidine kinase gene (selected by ganciclovir), etc.; toxin genes, such as the diphtheria toxin (DT) A gene, etc.; or combinations of these genes.

So that Cav1-reporter expression can be reinstated at a selected time, the present invention features recombinase target sites flanking the 5' and 3' ends of the open reading frame of the selectable marker expression construct. The recited recombinase target sites refer to nucleotide sequences which undergo recombination (e.g., DNA cross-over and exchange) when catalyzed by a recombinase, such as Cre, Flp or another member of the Int family of recombinases (see, e.g., Argos, et al. (1986) *EMBO J.* 5:433). Suitable target sequences include, for example, the well-known loxP sequences recognized by Cre recombinase, and the frt sequences recognized by Flp recombinase.

In this respect, the term "recombinase" refers to any recombinase which catalyzes a site-specific recombination at a corresponding target site thereby excising the marker expression cassette from the Cav1 open reading frame and restoring Cav1-reporter protein expression. Suitable recombinases include, for example, Cre recombinase (Sauer, et al. (1993) *Methods in Enzymology* 225:898), Flp recombinase (Buchholz, et al. (1996) *Nucl. Acids Res.* 24:4256-4262; Buchholz, et al. (1998) *Nat. Biotechnol.* 16:657-662), the R recombinase of *Zygosaccharomyces rouxii* pSR1, the A recombinase of *Kluyveromyces drosophilarium* pKD1, the A recombinase of *Kluyveromyces waltii* pKW1, the integrase λ Int, the recombinase of the GIN recombination system of the Mu phage or a variant thereof. For example, in many embodiments, the Cre/LoxP system is interchangeable with the FRT/FLP system, which has also been demonstrated to work in mice. Indeed, the Cre-loxP system has been routinely used to direct site-specific DNA recombination in transgenic animals (see, e.g., Orban, et al. (1992) *Proc. Natl. Acad. Sci. USA* 89(15):6861-5). Other recombinases which may be adapted to the mouse herein include Rs, RAG1/2, etc. In addition, alternative recombinases with novel specificity may be generated using established mutation and selection protocols, e.g. Buchholz, et al. (2001) *Nat. Biotechnol.* 19(11):1047-52.

Transgenic mice of the invention can be obtained by preparing vectors harboring the coding sequence of the Cav1-reporter disrupted by a selectable marker expression construct, wherein said vector is suitable for heterologous or homologous recombination. When homologous recombination is desired to create a Cav1 knock out, desirably, the vector contains Cav1 gene sequences sufficient to permit the homologous recombination of the vector into at least one allele of the Cav1 gene resident in the chromosomes of the target or recipient cell (e.g., ES) cells. The insertion of nucleic acids into vectors can be carried out in vitro by using conventional DNA recombination techniques (Sambrook, et al. (1989) *Molecular Cloning*, Cold Spring Harbor Laboratory Press). Vectors for creating transgenic mice are well-known in the art and readily available from various commercial sources.

The introduction of the vector into cells, e.g., embryonic stem (ES) cells or somatic cells, can be performed by methods well-known to those skilled in the art, for example, the electroporation method, calcium phosphate co-precipitation method, protoplast or spheroplast fusion method, lipofection or DEAE-dextran-mediated transfection. Such introduction results in insertion of the Cav1-reporter nucleic acids at some random or otherwise designated location in the genome, or alternatively, recombination occurs between the endogenous Cav1 gene and the corresponding region of the recombination vector in some population of the cells thereby creating a knock out or gene disruption. In this manner, the endogenous wild-type gene is substituted with the gene having the genotype constructed in the vector. Thus, it is possible to obtain cells having a Cav1-reporter gene in which a selectable marker gene and/or loxP sequences have been introduced into the endogenous Cav1 locus.

In so far as the vector contains a selectable marker expression construct, cells can be selected based upon acquisition of the marker. For example, when a drug-resistance gene is used as the marker, cells in which the desired recombination has taken place can be selected by culturing the cells in the presence of the drug at a lethal level subsequent to the introduction of vector. In addition to the selectable marker expression construct that inactivates the Cav1 transgene, the vector may also contain one or more additional selectable marker genes. When more than one selectable marker gene is employed, desirably one marker is a positive selectable marker (e.g., the neo gene) and the second is a negative selectable marker (e.g., the Herpes simplex virus tk (HSV-tk) gene).

Desirably mice cells which have integrated said Cav1-reporter coding sequence are selected and implanted in mice embryos leading to adult mice harboring the transgene. According to one embodiment, ES cells are used and injected into blastocysts to prepare chimera embryos. The chimeric embryos are then transferred into the horn of uterus of pseudopregnant mammals to obtain newborns. The blastocysts to be used for the injection can be obtained by perfusing the uterus of a pregnant female. To determine whether or not the ES cell has been incorporated in the developing embryo after the creation of an individual mammal, it is preferable to select the type of blastocyst that gives different external characteristics (for example, fur color) to distinguish the origin of a cell, whether it is derived from the ES cell or blastocyst, in the created animal. Subsequently, newborns are obtained by mating the resulting chimeric animal with an animal of an appropriate strain of the same species.

When somatic cells other than ES cells are used in the present invention, it is possible to create a knock-in animal by using techniques for creating somatic cell cloned animals. For example, Cav1-reporter nucleic acids harboring the selectable marker expression construct are introduced into cells other than ES cells, e.g., fibroblast cells; an animal carrying the Cav1-reporter nucleic acids is created from this cell by using the method for creating somatic cell cloned animals (Wilmut, et al. (1997) *Nature* 385:810-803; Wakayama, et al. (1998) *Nature* 394:369-374; and the resulting animal newborn carrying the Cav1-reporter corresponds to the F1 mouse of the method using the ES cell, and can be used thereafter according to a same manner as the ES cell. Transgenic mice obtained via ES cell or somatic cell methods have the phenotype Cav1-reporter$^{+/-}$/Marker$^{+/-}$ or Cav1-reporter$^{+/+}$/Marker$^{+/+}$.

For conditional expression of the Cav1-reporter transgene, the present invention also embraces a transgenic mouse expressing Cav1 in a time- or tissue-specific manner. Such a transgenic mouse can be obtained by mating a Cav1-reporter$^{+/-}$/Marker$^{+/-}$ or Cav1-reporter$^{+/+}$/Marker$^{+/+}$ transgenic mouse to a mouse whose genome contains a nucleic acid molecule encoding a recombinase under the control of a time-specific, phase-specific and/or tissue-specific promoter. The mating of a transgenic mouse having regulated recombinase expression with an Cav1-reporter$^{+/-}$/Marker$^{+/-}$ or Cav1-reporter$^{+/+}$/Marker$^{+/+}$ animal results in time-specific, phase-specific and/or tissue-specific removal of the marker expression construct from the Cav1 transgene thereby allowing for expression of the Cav1-reporter fusion protein.

Transgenic mice having regulated recombinase expression can be obtained by the methods disclosed herein. It is contemplated that any time-specific, phase-specific and/or tissue-specific promoter can be employed to regulate expression of the recombinase and hence excision of the marker expression construct. The selection of the promoter used will be dependent upon the analysis to be conducted. In this respect, the wild-type caveolin-1 promoter can be employed to analyze wild-type expression of caveolin-1. In addition, it is contemplated that the promoter can be constitutive, to determine the effects of constitutive Cav1 expression; or inducible (e.g., the metallothionein promoter, tet promoter, or a hormone inducible promoter) to control expression of Cav1 in a time-specific manner by external stimuli. Additional exemplary promoters of use in this invention include, but are not limited to, the Tie2 promoter (Minami, et al. (2003) *Arterioscl. Thromb Vascular Biol.* 23:2041), which provides endothelial-specific expression and the Adipocyte Fatty Acid Binding Protein (aP2) promoter (Rival, et al. (2004) *J. Pharmacol. Exp. Therap.* 311:467-475), which provides adipocyte-specific expression.

In addition to the time- and tissue-specific analysis of Cav1 expression, the knock-in mice of the invention find application in developing therapeutics for the treatment of a variety of diseases in which Cav1 or caveolae have been implicated. For example, a test compound is administered to the knock-in mouse of the present invention, and the influence of the compound on Cav1 expression and/or a particular phenotype is tested to select compounds exhibiting desired effects. Furthermore, cells prepared from knock-in mouse can be used for developing therapeutics. For example, cells are prepared from embryos and such from knock-in mice of the present invention, and then a test compound is added to the cells to determine the influence of the compound on Cav1 expression or other phenotype thereby selecting compounds exhibiting the desired effect. The cells may be primary culture cells or established cell lines. The compounds screened are candidates for pharmaceutical agents.

In so far as up-regulation of Cav1 has been shown to provide protection against lung fibrosis (U.S. patent application Ser. No. 20090075875), the transgenic mouse of the invention can be used in the identification of agents for use in the treatment of lung fibrosis. Similarly, agents that elevate Cav1 expression levels have been shown to reduce glucosylceramide accumulation (U.S. patent application Ser. No. 20080132508). Thus, the transgenic mice of the invention can be used in the identification of agents useful in the treatment of diabetic retinopathy. Cav1 expression has also been shown to increase in metastatic human prostate cancer cells as compared to primary prostate tumors (U.S. patent application Ser. No. 20050036986). Accordingly, certain cancers may be treated by suppressing expression of the Cav1 gene in metastatic cells or cells predisposed to metastasis. Thus, agents inhibiting the expression of Cav1 can also be identified using the transgenic mouse of the invention.

The animal testing herein can also be supplemented and confirmed by testing on human subjects. However, the present animal models allow the testing of a large number of compounds, both by the methods described above and other methods known in the art, in a system similar in many important respects to that in humans.

The invention is described in greater detail by the following non-limiting examples.

Example 1

Generation of Mouse Line

The BAC clone containing the mouse Cav1 exon 3 was obtained from the Sanger Center, UK. A targeting construct was generated by recombination in bacteria, wherein the GFP gene was inserted in-frame with Caveolin 1 followed by a Neomycin expression cassette (the neomycin gene driven by the PGK promoter), wherein said cassette was flanked by loxP recombination sites. The Neomycin expression cassette disrupted the Cav1 mRNA resulting in a Cav1 null allele, allowed for selection of mutant ES cell clones, and destabilized the Cav1-GFPp mRNA thereby sharply decreasing its expression. A targeting plasmid was recovered and linearized. The construct was electroporated into V6.5 ES cells and candidate recombinants were selected antibiotic resistance. The resistant clones were screened for homologous recombination by Southern blot analysis. Two clones (#20 and #96) were aggregated with mouse blastocysts to obtain chimaera. Chimaera, detected by their agouti coat color, were crossed first with wild-type mice to check for germline transmission. Cav1-GFP$^{+/-}$; Neo$^{+/-}$ mice are viable, fertile and did not exhibit any overt phenotype.

The offspring (genotype Cav1-GFP$^{+/-}$; Neo$^{+/-}$) were then crossed with CMV-Cre transgenic mice (The Jackson Laboratory) to excise the Neomycin expression cassette and obtain Cav1-GFP$^{+/-}$; Neo$^{-/-}$ mice (Cav1-GFP mice). Equal amounts mouse lung total membrane protein from wild type and three Cav1-GFP mice were resolved by 12% SDS-PAGE, transferred to PVDF membrane and blotted with anti-caveolin 1 antibodies. The Cav1-GFP fusion protein was detected by the anti-Cav1 antibody at the expected molecular weight of 40 kD. The resulting Cav1-GFP$^{+/-}$; Neo$^{-/-}$; CMV-CRE$^{+/-}$ mice expressed Cav1-GFP at physiological levels in all the cells expressing Caveolin 1. However, endogenous Cav1 levels were diminished in Cav1-GFP mice, whereas endothelial markers CD31 and PV1 did not change.

Based on flow cytometry analysis of splenocytes, it was observed that Cav1-GFP was not expressed in mice that have no excision of the selectable marker cassette (i.e., PGK-Neo).

Confocal fluorescence microscopy analysis of unfixed and unstained heart sections from wild type mice showed a lack of fluorescence. In contrast, GFP fluorescence in Cav1-GFP mice exhibited a pattern reminiscent of blood vessels in the heart where Cav1 is specifically expressed. Moreover, Cav1-GFP was shown to colocalize with endogenous Cav1 in the lung, heart and pancreas and with endogenous CD31 as a marker of endothelial cells in the aorta, lung and pancreas. It was noted, however, that Cav1-GFP was expressed in other cell types as well.

To demonstrate tissue-specific expression, the Neomycin expression cassette was excised in a tissue-dependent manner in endothelial cells and adipocytes by crossing Cav1-GFP$^{+/+}$; Neo$^{+/+}$ with Tie2-Cre or adipocyte-specific aP2 promoter/enhancer-Cre transgenic mice from The Jackson Laboratory.

In addition, Cav1-GFP$^{+/+}$; Neo$^{+/+}$ mice with the endogenous Cav1 locus disrupted show the same phenotype as that published for Cav1 knockout mice.

What is claimed is:

1. A caveolin-1 heterozygous transgenic mouse whose genome comprises an endogenous caveolin-1 gene and a stably integrated exogenous nucleic acid molecule encoding caveolin-1 fused in-frame with a reporter protein, wherein said exogenous nucleic acid molecule further includes a selectable marker expression cassette flanked by recombinase target sites in such a manner that, upon exposure to recombinase, said selectable marker expression cassette is excised from said exogenous nucleic acid molecule and said transgenic mouse is viable and fertile and has a reduced level of endogenous caveolin-1 as compared to a wild-type mouse.

2. The transgenic mouse of claim 1, wherein the recombinase is Cre and the recombinase target sites are loxP sequences.

3. The transgenic mouse of claim 1, wherein the recombinase is Flp and the recombinase target sites are Frt sequences.

4. The transgenic mouse of claim 1, wherein the reporter protein is an autofluorescent protein.

5. The transgenic mouse of claim 1, wherein the selectable marker expression cassette is a neomycin expression cassette.

6. A method for generating a mouse expressing caveolin-1 in an endothelial or adipocyte-specific manner comprising mating the transgenic mouse of claim 1 to a mouse whose genome comprises a nucleic acid molecule encoding a recombinase under the control of an endothelial or adipocyte-specific promoter, thereby generating a mouse expressing caveolin-1 in an endothelial or adipocyte-specific manner.

7. A mouse produced by the method of claim 6.

* * * * *